(12) United States Patent
Baker et al.

(10) Patent No.: US 12,125,400 B2
(45) Date of Patent: Oct. 22, 2024

(54) PLUNGER SPEED CONTROL TRAINING SYSTEM AND METHOD

(71) Applicant: NOBLE INTERNATIONAL, INC., Orlando, FL (US)

(72) Inventors: Jeff Baker, Orlando, FL (US); Dinesh Venkata Koka, Winter Park, FL (US); Jeffery A. Lettman, Orlando, FL (US); Tingting Liu, Orlando, FL (US); Tomas Andrius Matusaitis, Chicago, IL (US); Sean Joel Corrigan, Chicago, IL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 1333 days.

(21) Appl. No.: 16/627,503

(22) PCT Filed: Jun. 28, 2018

(86) PCT No.: PCT/US2018/040148
§ 371 (c)(1),
(2) Date: Dec. 30, 2019

(87) PCT Pub. No.: WO2019/006210
PCT Pub. Date: Jan. 3, 2019

(65) Prior Publication Data
US 2020/0168124 A1    May 28, 2020

Related U.S. Application Data

(60) Provisional application No. 62/526,780, filed on Jun. 29, 2017.

(51) Int. Cl.
*G09B 23/28* (2006.01)
*A61M 5/31* (2006.01)
*A61M 5/315* (2006.01)

(52) U.S. Cl.
CPC ... *G09B 23/285* (2013.01); *A61M 2005/3121* (2013.01); *A61M 5/31528* (2013.01)

(58) Field of Classification Search
CPC ............ G09B 23/285; A61M 5/31528; A61M 2005/3121
(Continued)

(56) References Cited

U.S. PATENT DOCUMENTS

| 8,714,984 | B2 * | 5/2014 | Mach | A61M 5/20 434/272 |
| 2013/0204195 | A1 * | 8/2013 | Ekman | A61M 5/326 604/220 |

(Continued)

*Primary Examiner* — Jay Trent Liddle
*Assistant Examiner* — Alyssa N Brandley
(74) *Attorney, Agent, or Firm* — Timothy H. Van Dyke; Wolter, Van Dyke, Davis, PLLC

(57) ABSTRACT

In an embodiment, an injection simulation device is provided. The injection simulation device may include a housing defining an opening, the housing having a proximal end and a distal end, a plunger movable relative to the housing, the plunger comprising a first interfacing portion, and distal movement of the plunger initiates an injection simulation, a rotatable component comprising a proximal end and a distal end, and an aperture extending between the proximal and distal ends of the rotatable component for receiving a portion of the plunger, rotatable component comprising a second interfacing portion for interfacing with the first interfacing portion to rotate the rotatable component when the plunger is moved toward the proximal or distal end of the housing. The injection simulation device may further include a stationary component defining a cavity for receiving the rotatable component, the cavity comprising a fluid, wherein movement of the plunger causes rotational and axial movement of the rotatable component, such that an interface between the rotatable component and the stationary component causes an increase in resistance during distal movement (Continued)

of the plunger, and a decrease in resistance occurs upon proximal movement of the plunger.

9 Claims, 13 Drawing Sheets

(58) Field of Classification Search
USPC .......................................................... 434/262
See application file for complete search history.

(56) References Cited

U.S. PATENT DOCUMENTS

| | | | |
|---|---|---|---|
| 2015/0235571 A1* | 8/2015 | Alexandersson . | A61M 5/31501 |
| | | | 434/262 |
| 2016/0335920 A1* | 11/2016 | Bendek ................ | G09B 23/285 |
| 2017/0337845 A1* | 11/2017 | Su ........................ | G09B 23/285 |
| 2020/0101227 A1* | 4/2020 | Mach ................... | G09B 23/285 |

* cited by examiner

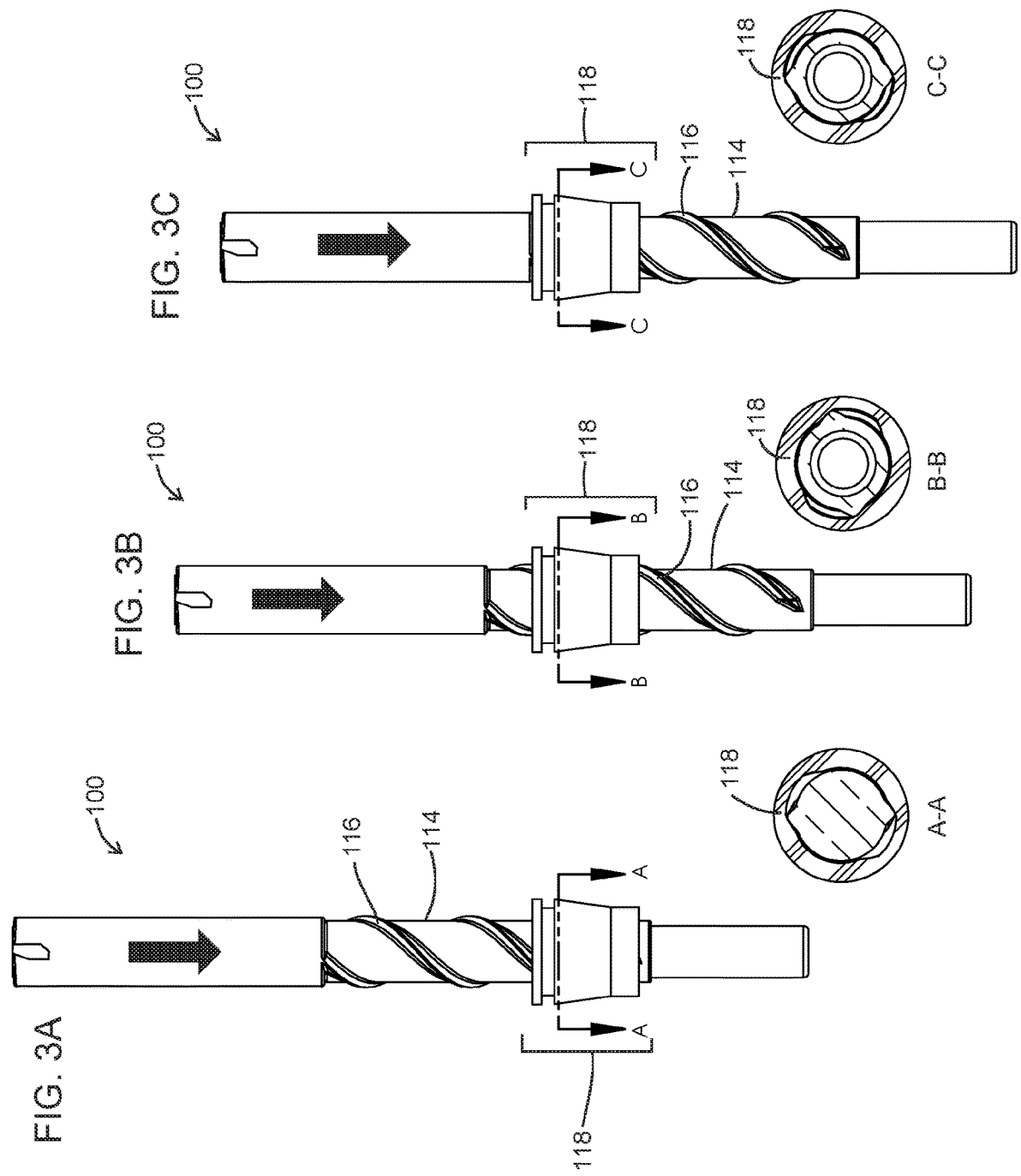

PLUNGER SPEED CONTROL TRAINING SYSTEM AND METHOD

BACKGROUND

Many medications are taken into the body by way of an injection. An injection device typically includes a housing, a plunger and a needle. When a force is applied to a plunger by a mechanical means, such as in an auto injector or manually by the person administering the injection, the medicament is delivered through the needle into the target area of the subject. A resistance is caused by delivery of a fluid medicament from an injection device. The amount of time required to provide an injection is dictated, in part, by the amount of resistance due to the delivery of the fluid medicament. Medicaments include different viscosities which also contributes to the amount of time required to perform an injection. Injection training devices are used to train users to deliver injections. There is often a fear associated with injecting a subject. Injection training devices are used to calm that fear by allowing a user to practice the injection process with a simulated injection device. With medications having different viscosities, and consequently, differing in terms of injection time, simulating the injection experience can be challenging. Moreover, with more medicaments becoming increasingly viscous, increasing delivery times, difficulty occurs in producing an injection training device for simulating a drug delivery device.

SUMMARY

In a first embodiment, an injection simulation device is provided. The injection simulation device may include a housing defining an opening, the housing having a proximal end and a distal end, a plunger movable relative to the housing, the plunger comprising a first interfacing portion, and distal movement of the plunger initiates an injection simulation, a rotatable component comprising a proximal end and a distal end, and an aperture extending between the proximal and distal ends of the rotatable component for receiving a portion of the plunger, rotatable component comprising a second interfacing portion for interfacing with the first interfacing portion to rotate the rotatable component when the plunger is moved toward the proximal or distal end of the housing. The injection simulation device may further include a stationary component defining a cavity for receiving the rotatable component, the cavity comprising a fluid, wherein movement of the plunger causes rotational and axial movement of the rotatable component, such that an interface between the rotatable component and the stationary component causes an increase in resistance during distal movement of the plunger, and a decrease in resistance occurs upon proximal movement of the plunger.

In a further embodiment, an injection simulation device for controlling the speed of a plunger movement is provided. The injection simulation device may include a housing defining an opening, and comprising a proximal end and a distal end, a plunger movable relative to the housing, the plunger comprising a first interfacing portion, and a rotatable component defining a channel for receiving the plunger, the rotatable component axially movable relative to the plunger, said rotatable component comprising a second interfacing portion configured to interface with the first interfacing portion during advancing or retracting of the plunger. The injection simulation device may further include a stationary component defining a cavity comprising a damping fluid, the cavity for receiving the rotatable component, wherein advancing the plunger in a distal direction causes rotational movement of the rotatable component, wherein that rotational movement is controlled by the damping fluid, increasing plunger resistance, and retracting the plunger in a proximal direction decreases resistance on the plunger.

In still a further embodiment, an injection simulation device including a housing defining a channel, the housing comprising a proximal end and a distal end is provided. The injection simulation device may include a plunger associated with and movable relative to the channel, the plunger comprising a proximal end and a distal end, and at least one protrusion member that interfaces with the housing, wherein the plunger moves in a distal and proximal direction within the channel, and wherein a differential force is required to move the plunger in the distal direction versus the proximal direction, wherein when the plunger is moved in the distal direction, the at least one protrusion member increases a friction during movement of the plunger in the distal direction.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 3A-C includes a partial side view of a portion of an injection simulation device embodiment shown in FIG. 1, showing sequential steps in use of the device.

DETAILED DESCRIPTION

Figure 1:
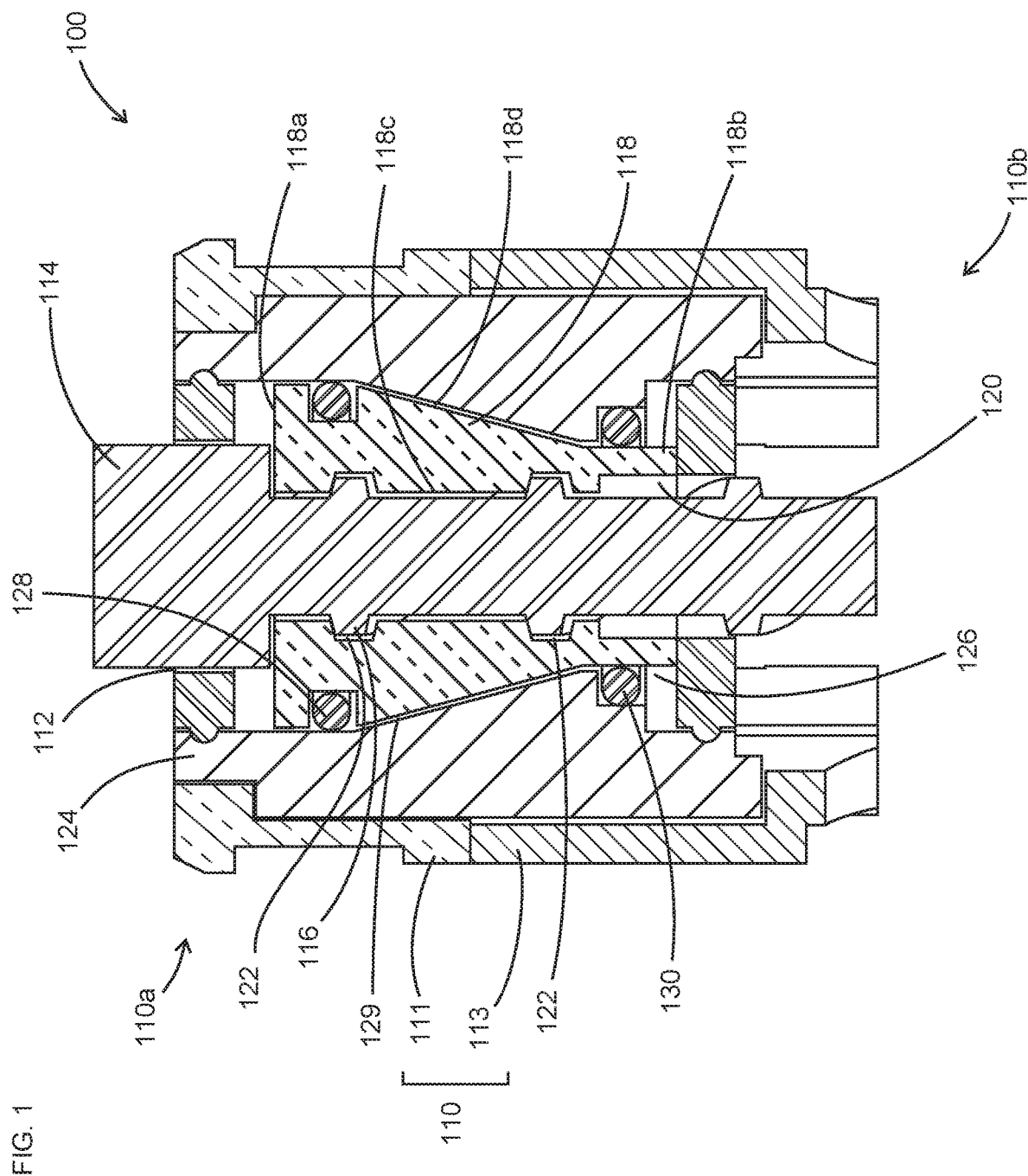
FIG. 1 includes a partial, cross-sectional view of an injection simulation device embodiment including a rotatable component and a stationary component.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

The term "medicament" as used in describing the various embodiments of this invention includes an injectable liquid medicine, medication, drug, pharmaceutical, prescriptive, agent, antidote, anti-venom, hormone, stimulant, vasodilator, anesthetic, nutritional supplement, vitamin and/or mineral compound, saline solution, biological, organic compound, genetically and/or chemically modified protein and/or nucleic acids, or other liquid that is adapted to be injected into the tissue of a subject.

The term associated or association, as used herein, includes but is not limited to direct and indirect attachment, adjacent to, in contact with, partially or fully attached to, and/or in close proximity therewith. The term "in conjunction with" as used herein includes but is not limited to synchronously or near synchronous timing, the phrase may also include the timing of outputs, where one output directly follows another output.

As used herein, the terms "subject", "user" and "patient" are used interchangeably. As used herein, the term "subject" refers to an animal, and most preferably a human.

The term "annular member" as used herein, may include o-rings or biasing members, including springs, the annular member may include a canted coil spring in one non-limiting embodiment.

Many of the injection devices on the market require patients to self-administer injections, for example, via a pre-filled syringe in a non-limiting example. Other injection devices used for self-administration may include an autoinjector, for example. Between injection devices, and between medicaments being injected, there is often a varying amount of force is required to deliver an injection. The inventors herein have discovered a device, wherein the force required to deliver an injection can be simulated by an injection training or injection simulation device. In this manner, a user may familiarize his or herself with the forces required to use a particular injection device, and with said device, deliver an effective injection. With the injection simulation device described herein, a user may become familiar with the look and feel of an injection device via use of the injection simulation device, before using the injection (drug delivery) device to deliver a medicament. Consequently, the importance of replicating the forces noted during use of the medicament-containing injection device during use of the simulated device. Inventors provide herein, a number of embodiments developed to provide this capability. Forces required to actuate an injection device may depend on a number of factors, including, but not limited to the various components of the device and their interactivity, as well as the viscosity of the medicament being delivered therefrom, for example. The forces to reset such a device may be lower than the forces required to actuate and deliver an injection via such a device, in some non-limiting embodiments.

Consequently, in embodiments provided herein, an injection simulation device for simulating the forces encountered during use of a medicament-containing injection device is provided. In some non-limiting embodiments, the actuation and/or medicament delivery force is greater than the force required to reset the injection simulation device. During the course of an injection with a prefilled syringe, or other non-autoinjector device, the forces encountered often include a deformation force when the target area contact tissue is deformed prior to its traversal by the needle, a puncture force which occurs when the needle traverses the skin of a user, for example, an insertion force and/or a breakaway force or a break out glide force.

Various forces may also be encountered during the use of an autoinjector. An activation force is required to trigger the device, and often a reaction force or recoil may occur following the activation force. Simulating these forces is monumental in providing an effective patient training experience. When a patient is able to train using a training device that accurately simulates the medicament-containing injection device, the patient may then use the medicament-containing injection device with a higher chance of success in obtaining a correct dose of the medicament, and any fear or anxiety associated with administering and/or receiving the injection may be minimized.

In some non-limiting embodiments, the force(s) required to actuate the injection simulation device may include a force of between 0.5 N (Newtons) and 45 N, including any 0.5 N increment there between. In another non-limiting embodiment, the force(s) required to actuate the injection simulation device may include a force of between 5 N and 35 N, including any 0.5 N increment there between.

In a first embodiment shown in the partial, cross-sectional view of an injection simulation device 100 is provided in FIG. 1, including a housing 110 defining an opening 112, the housing 110 including a proximal end 110a and a distal end 110b. The device 100 includes a plunger 114, movable relative to the housing 110, the plunger 114 including a first interfacing portion 116, such that distal movement of the plunger 114 initiates an injection simulation. The first interfacing portion 116 may interface with a second interfacing portion 122 during proximal and/or distal movement of the plunger 114. The device 100 includes a rotatable component 118 having a proximal end 118a and a distal end 118b, and an aperture 120 extending between the proximal and distal ends 118a, 118b of the rotatable component 118 for receiving a portion of the plunger 114. The rotatable component 118 may include the second interfacing portion 122 for interfacing with the first interfacing portion 116 to rotate the rotatable component 118 when the plunger 114 is moved toward the proximal or distal end of the housing 110a, 110b. The device 100 includes a stationary component 124 defining a cavity 126 for receiving the rotatable component 118, the cavity 126 comprising a fluid 129. The fluid 129 may be maintained within the cavity by way of a first sealing member 128 and a second sealing member 130, to prevent leakage of fluid 129 from between the rotatable component 118 and the stationary component 124.

Figures 2A, 2B:
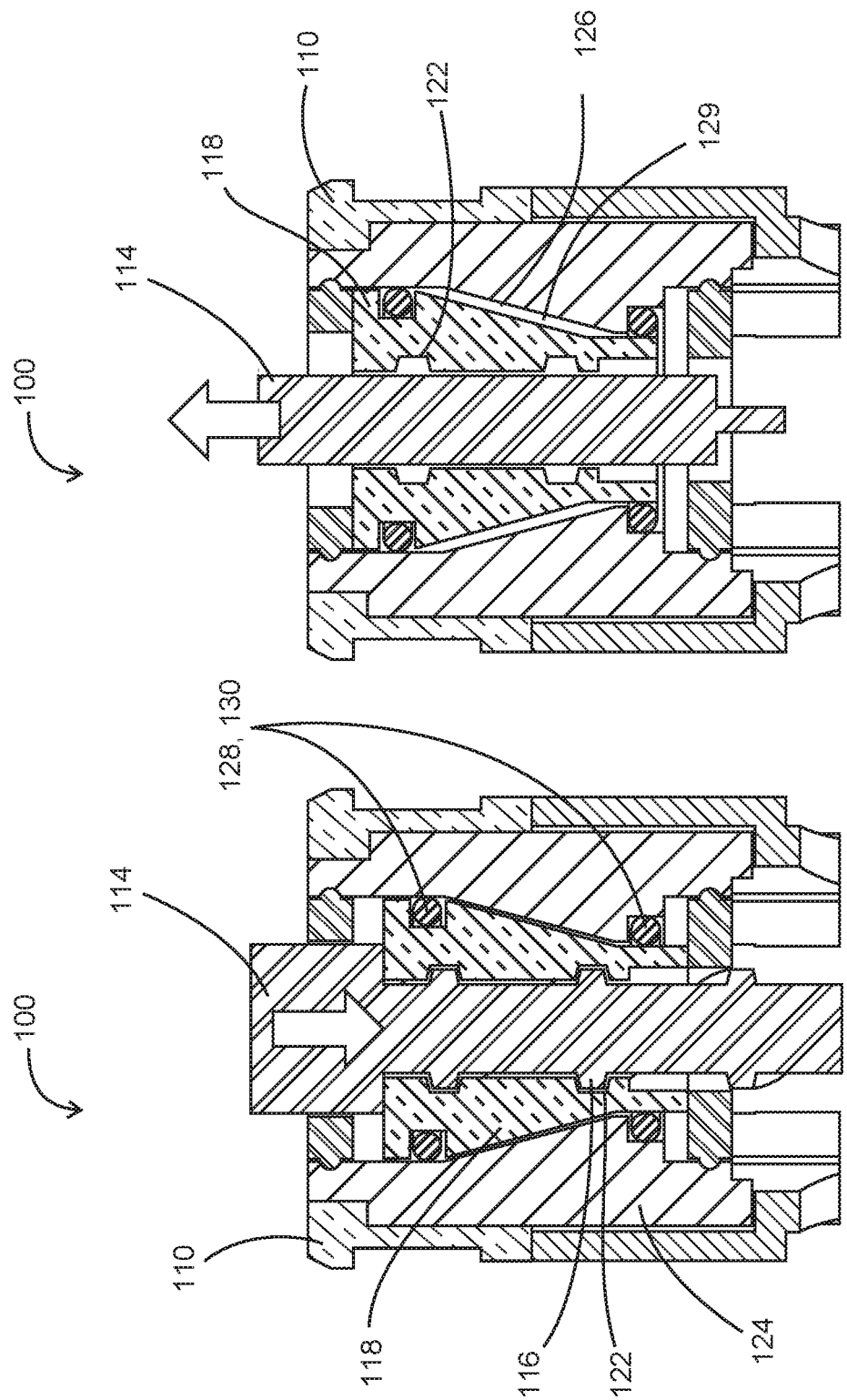
FIG. 2A-FIG. 2B includes a partial, cross-sectional view of the injection simulation device embodiment shown in FIG. 1 during use of the device.

Movement of the plunger 114 causes rotational and axial movement of the rotatable component 118 as can be seen in FIGS. 2A-2B, such that an interface between the rotatable component 118 and the stationary component 124 may cause an increase in resistance during distal movement of the plunger 114, and a decrease in resistance during proximal movement of the plunger 114. The resistance may additionally, or alternatively, be controlled via the fluid 129, by adding fluid between the components, or by varying the viscosity of the fluid 129 between the components of the device 100. Fluid 129 may be used between other components of the device 100 in order to control speed and/or function of the device 100.

In a further embodiment, as aforementioned, the device 100 may include a first sealing member 128 adjacent to the proximal end of the rotatable component 118a. In a further embodiment, the device 100 may include a second sealing member 130 adjacent to the distal end of the rotatable component 118b for sealing the cavity 126. In some embodiments, adjusting the viscosity of the fluid within the cavity 126 alters the resistance on the movement of the plunger 114 between the proximal end of the housing 110a and the distal end of the housing 110b (proximal and distal ends shown in FIG. 1). In one non-limiting embodiment, an increase in the viscosity of the fluid 129 increases the resistance on the distal movement of the plunger 114. In one non-limiting embodiment, the fluid 129 includes a damping material. In a further non-limiting embodiment, the damping material may include a damping grease. As can be seen in FIG. 2A, as the plunger 114 is moved in a distal direction, the interface between the first interfacing portion of the plunger 116 and the second interfacing portion of the rotatable component 122 causes the rotatable component 118 to rotate. In an alternative embodiment, the rotatable component 118 may be stationary, and the plunger 114 may rotate relative thereto, wherein the fluid 129 may be provided between the rotatable component 118 and the plunger 114, in one non-limiting example. In FIG. 2B, a portion of the cavity 126 is visible between the rotatable component 118 and the stationary component 124, where the fluid 129 may reside. During proximal movement of the plunger 114, the interface between the rotatable component 118 and the stationary component 124 may decrease, and the resistance on the plunger 114 movement, may likewise decrease.

As can be seen in FIGS. 2A-2B, in one non-limiting embodiment, the surface of the stationary component 124 which interfaces with the rotatable component 118 is complementary in shape to the rotatable component 118 surface. This further contributes to the effects of the movement of the components relative to one another, and to the resistance created by such movement. Furthermore, the surfaces of the various components of the device described herein may be textured so as to control resistance on different components of the device 100 when the components interface with one another.

In a further embodiment, the viscosity of the fluid 129 may control the speed of rotation of the rotatable component 118 as the plunger 114 is advanced within the aperture 120.

In one embodiment, distal movement of the plunger 114 may increase an interface between the rotatable component 118 and the stationary component 124. In an embodiment, proximal movement of the plunger 114 may decrease an interface between the rotatable component 118 and the stationary component 124. In a further embodiment, the device 100 includes a biasing member 132 associated with the plunger 114 to effect movement of the plunger (not shown in FIG. 1).

In one non-limiting embodiment, the outer surface profile of the rotatable component 118 comprises a conical shape, and the inner surface profile of the stationary component 124 comprises a conical shape complementary to the outer surface profile of the rotatable component 118, such that one or both of the components may rotate relative to one another during operation of the device 100. In another embodiment, the housing 110 comprises a first housing component 111 and a second housing component 113. The housing components 111, 113 may be affixed to one another, and may be formed as one component.

FIG. 3A-3C shows an embodiment of the device 100, wherein distal movement of the plunger 114 causes helical rotation of the rotatable component 118 may as the rotatable component 118 rotates, the first and second interfacing portions 116, 122 interface, to cause the rotatable component 118 to move relative to the plunger 114, or vice versa, such that in the most proximal position of the plunger 114, the rotatable component 118 is disposed on a portion of the plunger shaft.

Figure 4:
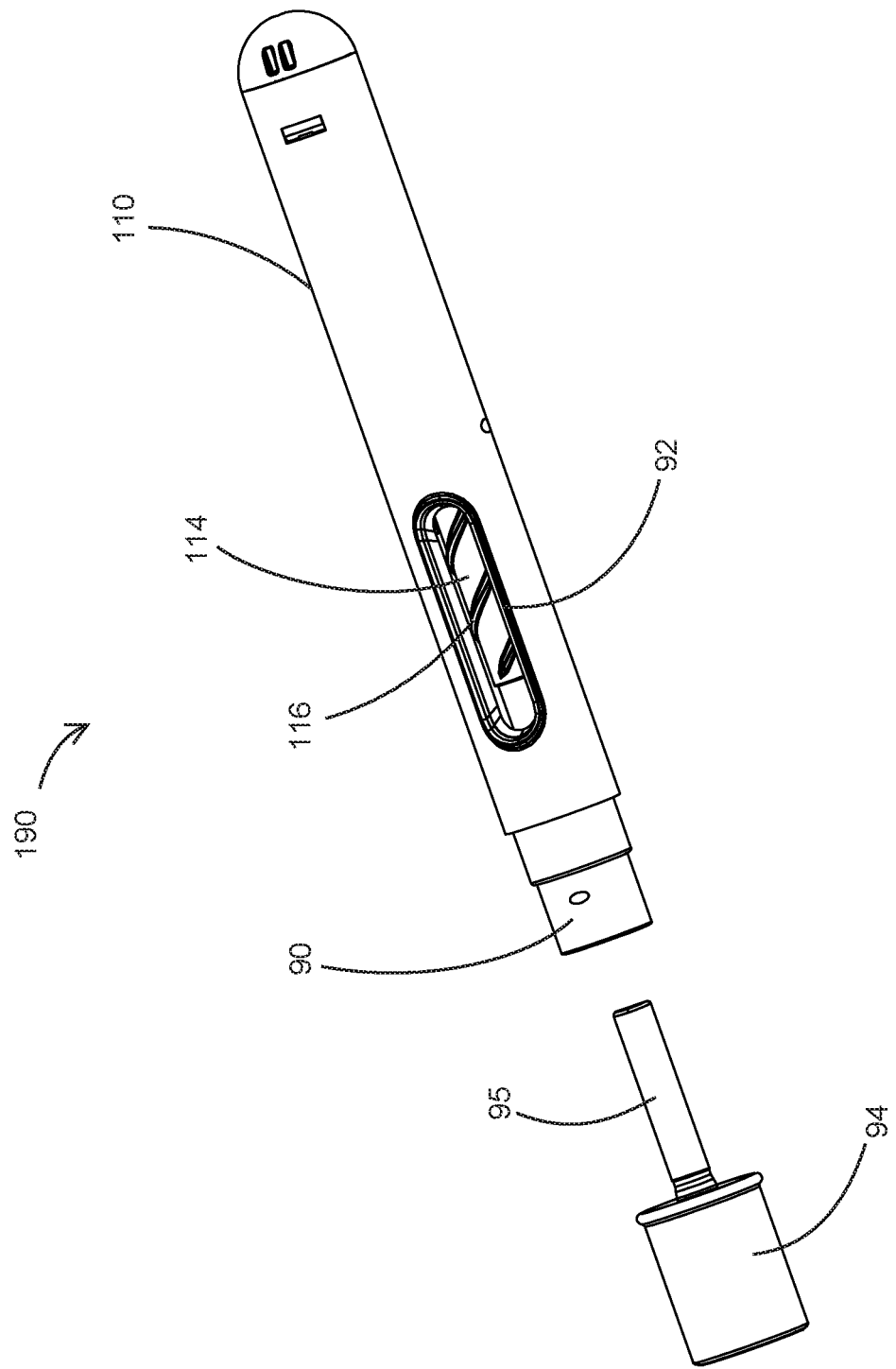
FIG. 4 includes a side view of an injection simulation device embodiment, comprising the rotatable component and the stationary component, with a reset cap removed from the device.

In an embodiment shown in FIG. 4, an injection simulation device 100 for controlling the speed of a plunger 114 movement, including a housing 110 defining an opening 92, the housing having a proximal end 110a and a distal end 110b. A plunger 114 is movable relative to the housing 110, the plunger 114 having a first interfacing portion 116. A rotatable component 118 defining a channel for receiving the plunger 114, the rotatable component 118 axially movable relative to the plunger 114, said rotatable component 118 comprising a second interfacing portion 122 configured to interface with the first interfacing portion 116 during advancing or retracting of the plunger 114. A stationary component 124 defining a cavity 126 having a damping fluid 129, the cavity 126 for receiving the rotatable component 118, in one non-limiting embodiment. Advancing the plunger 114 in a distal direction causes rotational movement of the rotatable component 118, wherein the rotational movement is controlled by the damping fluid 129, increasing plunger 114 resistance during advancing of the plunger 114 in a distal direction, and retracting the plunger 114 in a proximal direction decreases resistance on the plunger 114.

In a further embodiment, an increase in viscosity of the damping fluid 129 decreases the speed of rotation of the rotatable component 118 during distal movement of the plunger 114, and increases plunger resistance during distal movement.

In another embodiment, a decrease in viscosity of the damping fluid 129 increases the speed of rotation of the rotatable component 118 during distal movement of the plunger 114, and increases plunger resistance during distal movement. Proximal movement of the plunger 114 decreases the interface between the rotatable component 118 and the damping fluid 129 in the cavity 126 such that a resistance on the plunger 114 is decreased.

In a further embodiment, the device 100 may include one or more sealing members 128, 130, disposed in the cavity 126 to maintain the fluid 129 within the cavity. In another non-limiting embodiment, the one or more sealing members 128, 130 may be disposed between the rotatable component 118 and the stationary component 124 to seal the fluid 129 within the cavity 126.

Figure 7:
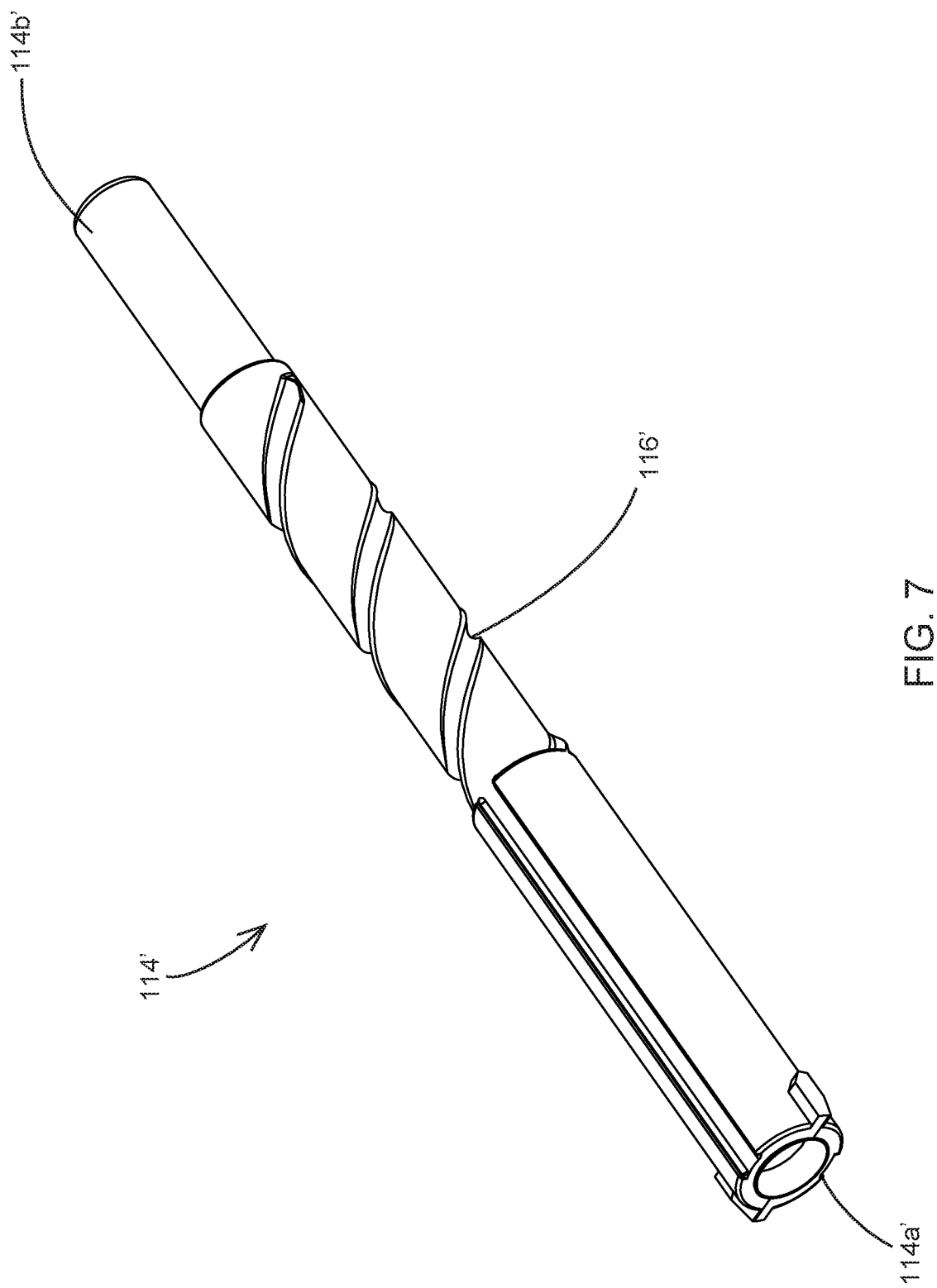
FIG. 7 provides a side view of an alternative plunger as shown in the device embodiment in FIGS. 6A-6B.

In another non-limiting embodiment, the first interfacing portion 116 may include a threaded portion or a threaded receiving portion, threaded receiving portion 116' is shown in FIG. 7. The first interfacing portion 116 comprises a threaded portion or a threaded receiving portion 116' as can be seen in FIGS. 3 and 7, respectively. In FIGS. 3A-C, the plunger comprises a first interfacing portion 116 having a threaded portion. In FIG. 7, the plunger comprises a first interfacing portion having a threaded receiving portion 116'. In the embodiment shown in FIG. 7, the first interfacing portion for receiving a threaded portion interfaces with a threaded portion of another component, for example, the rotatable component, to interface therewith.

In another non-limiting embodiment, the first interfacing portion 116 comprises a threaded portion, the second interfacing portion 122 comprises a threaded receiving portion. In still another embodiment, when the first interfacing portion 116 comprises a thread receiving portion, the second interfacing portion 122 comprises a threaded portion. In other non-limiting embodiments, the first interfacing portion may include a thread receiving portion, and the second interfacing portion may include a threaded portion.

Figure 5:
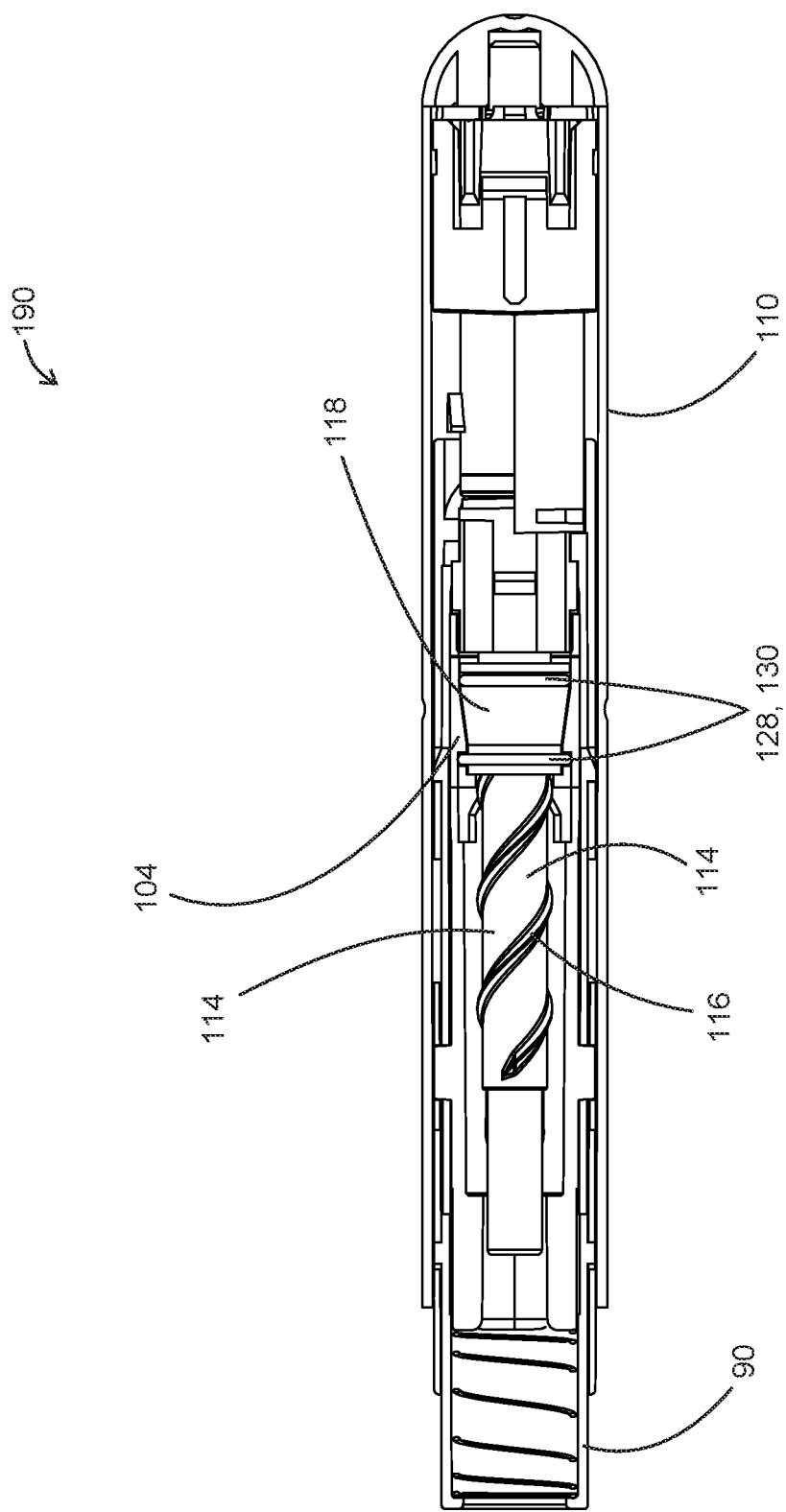
FIG. 5 is a cross sectional view of the injection simulation device embodiment shown in FIG. 4, without a reset cap.

FIGS. 4-5 and FIGS. 10-11 provide embodiments wherein the components are shown within an autoinjector device. FIG. 4 shows a perspective view of the autoinjector device 190 with a safety shield 90 associated with the device housing 110. FIG. 5 shows a cross sectional view of the autoinjector device 190. As seen in FIG. 4, a viewing window 92 provides a view into the housing 110 of the device 190, which may provide a visual output as to the stage of use or the condition of the device 190 and its internal components. A reset cap 94 is shown in FIG. 4, and can be used to reset the autoinjector training device 190 for a subsequent use by associating the reset cap 94 having a reset projection 95 with the distal end of the device housing 110, such that the reset projection 95 enters the device housing 110 distal end and may be used to reset one or more components of the device 190, including, for example, the plunger 114, the safety shield 90 or another component within the device 190.

Figure 6:
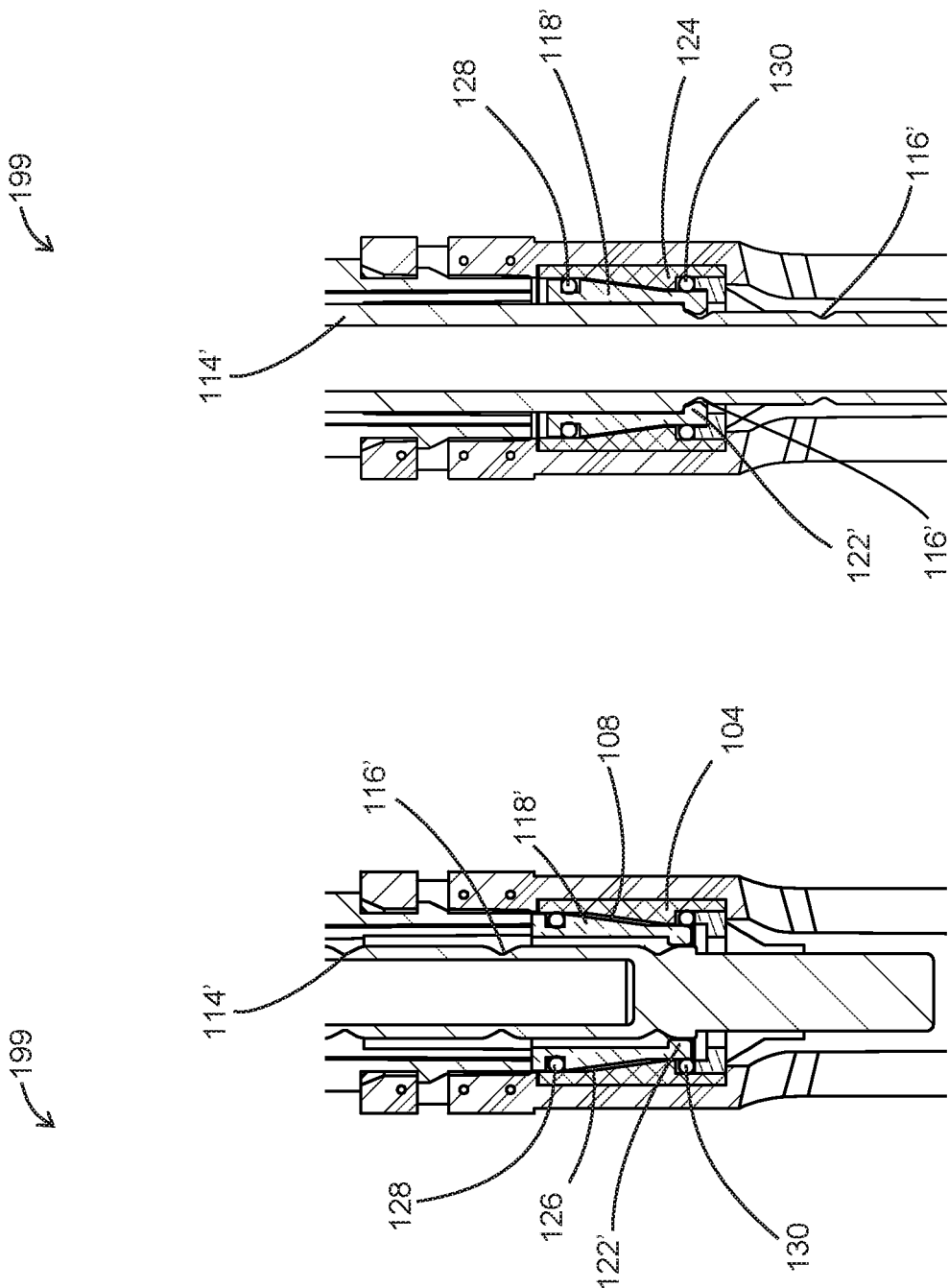
FIGS. 6A-6B provide partial cross-sectional views of an alternative injection simulation device embodiment, in a ready-to-fired (pre-use) position (FIG. 6A) and in a fired (post-use) position, (FIG. 6B).

In alternative embodiments such as the embodiment 199 shown in FIGS. 6A-6B, the first interfacing portion 116' may include a notch, and the second interfacing portion 122' may include a projection for interfacing with the notch as shown in FIGS. 6A-6B. Interfacing threaded and thread receiving portions may be interchangeable with grooves or notches and interfacing projections, however, in any of these non-limiting examples of interactivity between the components of the system, the components may be used to control the speed of the plunger. FIGS. 6A-6B provide a partial cross sectional view which show the sequential steps in use of an embodiment of the device 199. The embodiment 200 includes a plunger 114' having one or more first interfacing portions 116' thereon for interfacing with the second interfacing portions 122' of a rotatable component 118', respectfully. A first sealing member 128 is located near the upper end of the interface between the rotatable component 118' and a stationary component 124, which is associated with the housing. A second sealing member 130 is near the lower portion of the interface between the rotatable component 118' and the stationary component 124. The sealing members 128, 130 may include an o-ring in a non-limiting embodiment, or other type of sealing member known in the art, to prevent fluid from traversing the sealing member. A fluid 129 (not shown in FIGS. 6A-6B) is disposed between the rotatable component 118' and the stationary component 124, the fluid 129 controlling the speed at which the plunger 114' moves. Various viscosities of fluid 129 may be provided in the device 199, in order to speed up or slow down the movement of the plunger 114' as it is actuated, wherein the interface between the rotatable component 118' and the stationary component 124 is buffered by the fluid 129.

FIG. 6A shows the device in a ready to fire position, noting a possible position of the plunger 114' in a pre-fired position, and a notable gap (i.e., cavity) between at least a portion of the rotatable component 118' and the stationary component 124, wherein the fluid 129 may be contained. In the fired position shown in FIG. 6B, the plunger 114 has moved distally, and the gap (i.e., cavity) between the rotatable component 118' and the stationary component 124 is no longer visible. Movement of the plunger 114' causes the rotatable component 118' to rotate relative to the stationary component 124 via the interface between the first interfacing portion 116' and the second interfacing portion 122' and causes a pressure to be exerted on the plunger 114' during firing/actuation of the device, so as to narrow the space between the rotatable 118' and the stationary component 124, causing an increase in friction therebetween. This increase in friction further slows the movement of the plunger 114' by slowing the rotation of the rotatable component 118' in some embodiments.

FIG. 7, as aforementioned, provides a perspective view of a plunger embodiment 114' as embodied in the device 199 of FIGS. 6A-6B, the plunger 114' having a proximal end 114a' and a distal end 114b', and including a first interfacing portion 116' embodied as a notch or a thread receiving portion, as shown, for interfacing with the second interfacing portion of the device 199.

Figure 8:
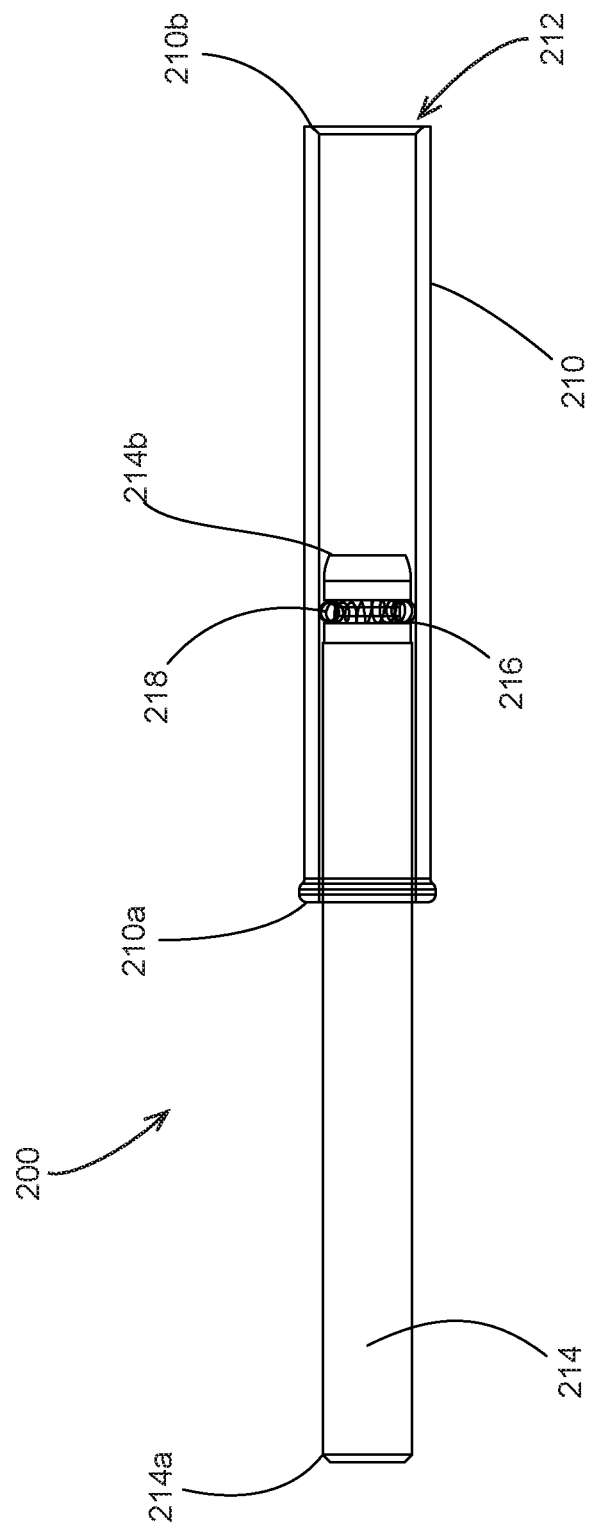
FIG. 8 provides a partial side view of an injection simulation device embodiment, showing a housing and a plunger slidable there within, the plunger having a protrusion member thereon.
Figure 9:
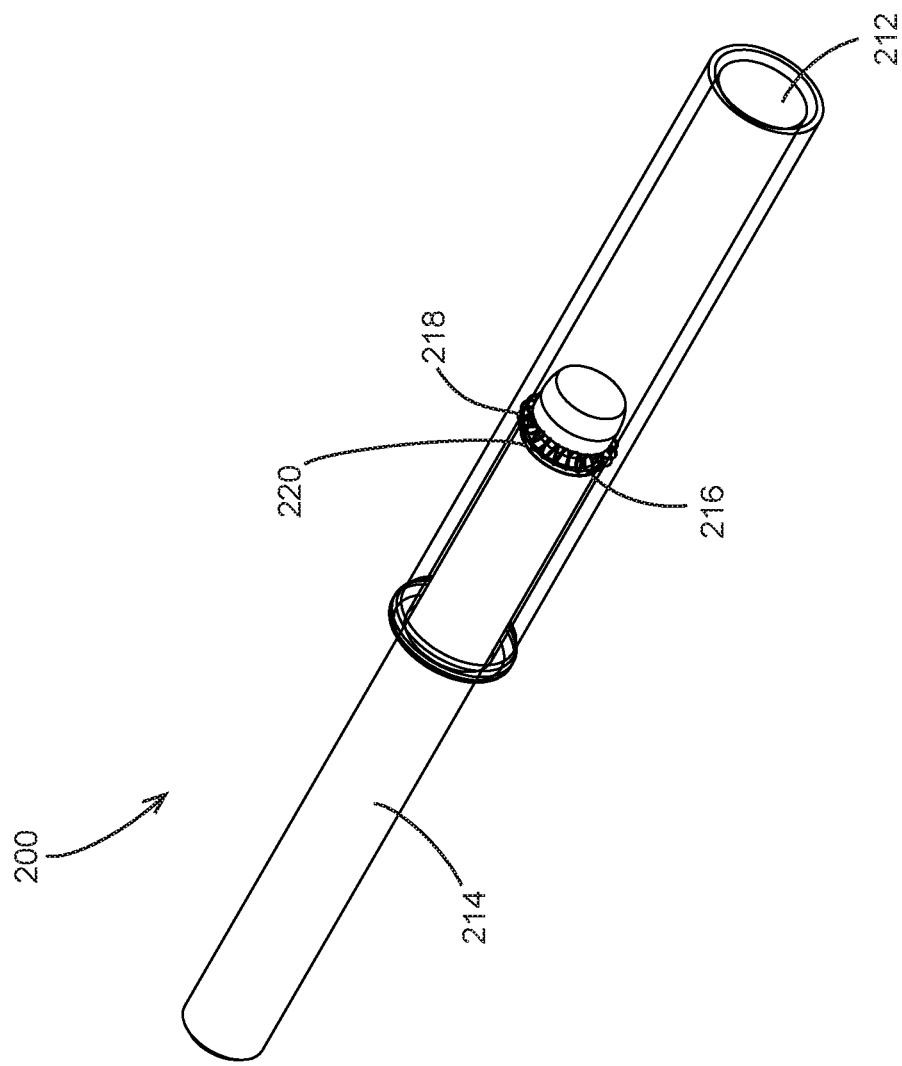
FIG. 9 is a perspective view of the device embodiment shown in FIG. 9.

In a further non-limiting embodiment shown in FIGS. 8-9, an partial cutaway view of injection simulation device 200 (showing only a portion of the housing and plunger in FIGS. 8-9) includes a housing 210 defining a channel 212, the housing 210 comprising a proximal end 210a and a distal end 210b, a plunger 214 associated with and movable relative to the channel 212, the plunger 214 comprising a proximal end 214a and a distal end 214b, and at least one protrusion member 218 that interfaces with the housing 210 as the plunger 214 moves relative to the housing 210. The plunger 214 moves in a distal and proximal direction within the channel 212, and wherein a differential force is required to move the plunger 214 in the distal direction versus the proximal direction. The plunger 214 may further include a groove 216, wherein the at least one protrusion member 218 rests within the groove 216 in a non-limiting embodiment. One non-limiting example of a plunger groove 216 and related protrusion member can be seen in FIGS. 12A-C.

In another embodiment, when the plunger 214 is moved in the distal direction, the at least one protrusion member 218 increases a friction on the plunger 214 during movement thereof. In one non-limiting embodiment, the at least one protrusion member 218 may be retained within the groove 216 of the plunger 214 during proximal and distal movement of the plunger 214. In another non-limiting embodiment, during distal movement of the plunger 214, the protrusion member 218 may slide relative to the plunger 214, out of the groove 216, increasing the diameter of the protrusion member 218, and causing an increase in friction on the distal movement of the plunger 214. Wherein upon proximal movement of the plunger 214, the protrusion member 218 may move back into the plunger groove 216, decreasing proximal movement of the plunger 214.

In a further embodiment, the protrusion member 218 is retained within the groove 216, and when the plunger 214 is moved in the proximal direction, the outer diameter of the at least one protrusion member 218 may decrease by reducing contact with the housing and decreasing friction during movement of the plunger 214 in the proximal direction. In another embodiment, when the plunger 214 is moved in the distal direction, an outer surface of the at least one protrusion member 218 is deformed. In another embodiment, the plunger 214 may include an annular member disposed within and movable relative to the groove 216, as aforementioned. In one embodiment, the protrusion member 218 is an annular member.

In still a further non-limiting embodiment, the groove 216 includes an annular member abutting surface on the supra-groove surface 220 (see FIGS. 12B-12C), to maintain the annular member within the groove 216 during distal movement of the plunger 214.

In another embodiment, a friction between the annular member and the housing 210 increases upon movement of the plunger 214 in the distal direction, increasing a resistance on the plunger 214. In still another embodiment, upon movement of the plunger 214 in the proximal direction, the annular member moves in to the groove 216, and a friction between the annular member and the housing decreases, decreasing a resistance on the plunger 214.

In a further non-limiting embodiment, the distal movement of the plunger 214 causes the annular member to expand laterally, increasing a resistance on the distal movement of the plunger 214. In yet another non-limiting embodiment, the annular member comprises a garter spring, a toroidal spring, or an annular shaped ring or seal.

Figure 10:
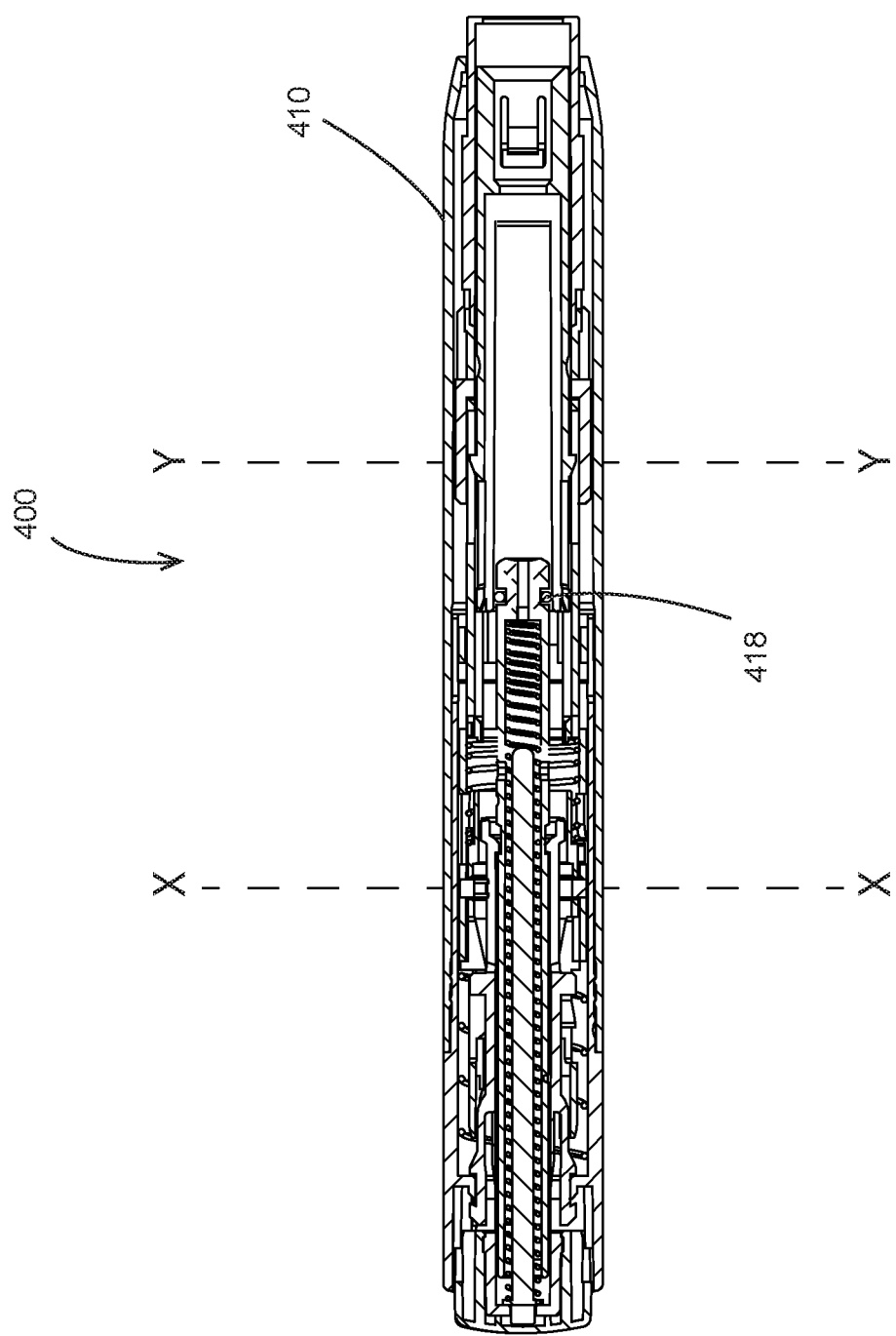
FIG. 10 provides a cross-sectional view of an injection simulation device embodiment, showing placement of a protrusion member within the device.
Figure 11:
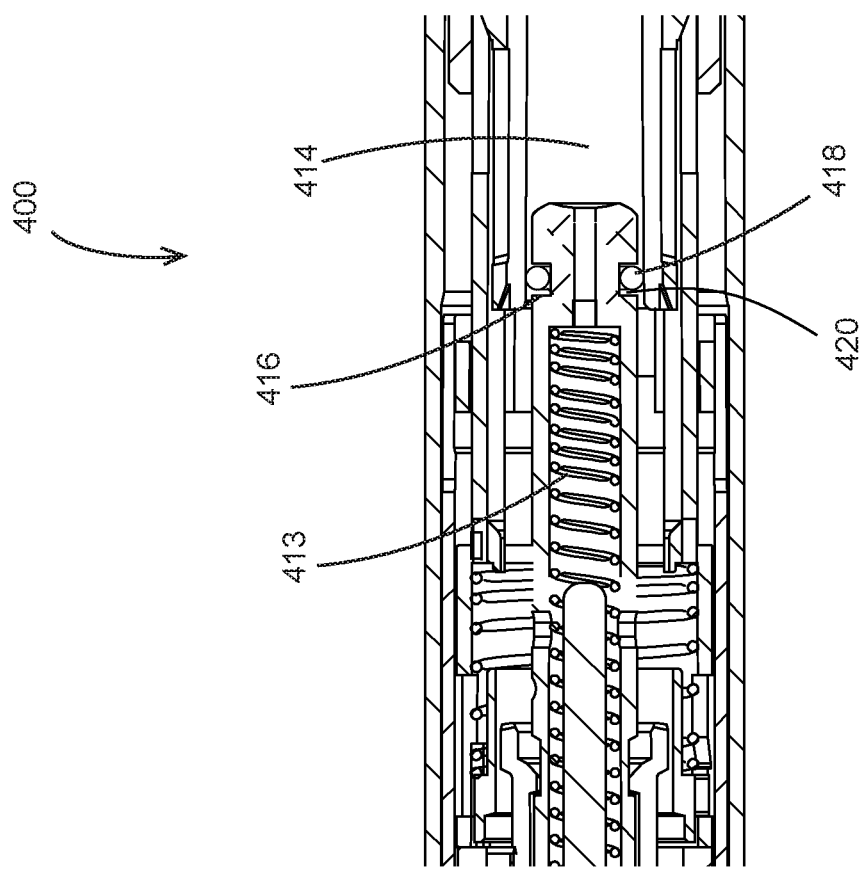
FIG. 11 provides a partial cross-sectional view of the embodiment shown in FIG. 10 between lines X-X, Y-Y.

FIG. 10 shows a cross-sectional view of an autoinjector device embodiment 400, showing an annular member 418 disposed there within. FIG. 11 is a partial cross-sectional view of the embodiment 400 shown in FIG. 10, taken at X-X and Y-Y. The groove 416 is visible in FIG. 11, as is the annular member 418, the supra-groove surface 420 for maintaining the annular member 418 within the groove 416 during movement of the plunger 414. A biasing member 413 associated with the plunger 414 is energized or activated in order to actuate the plunger 414.

Figure 12:
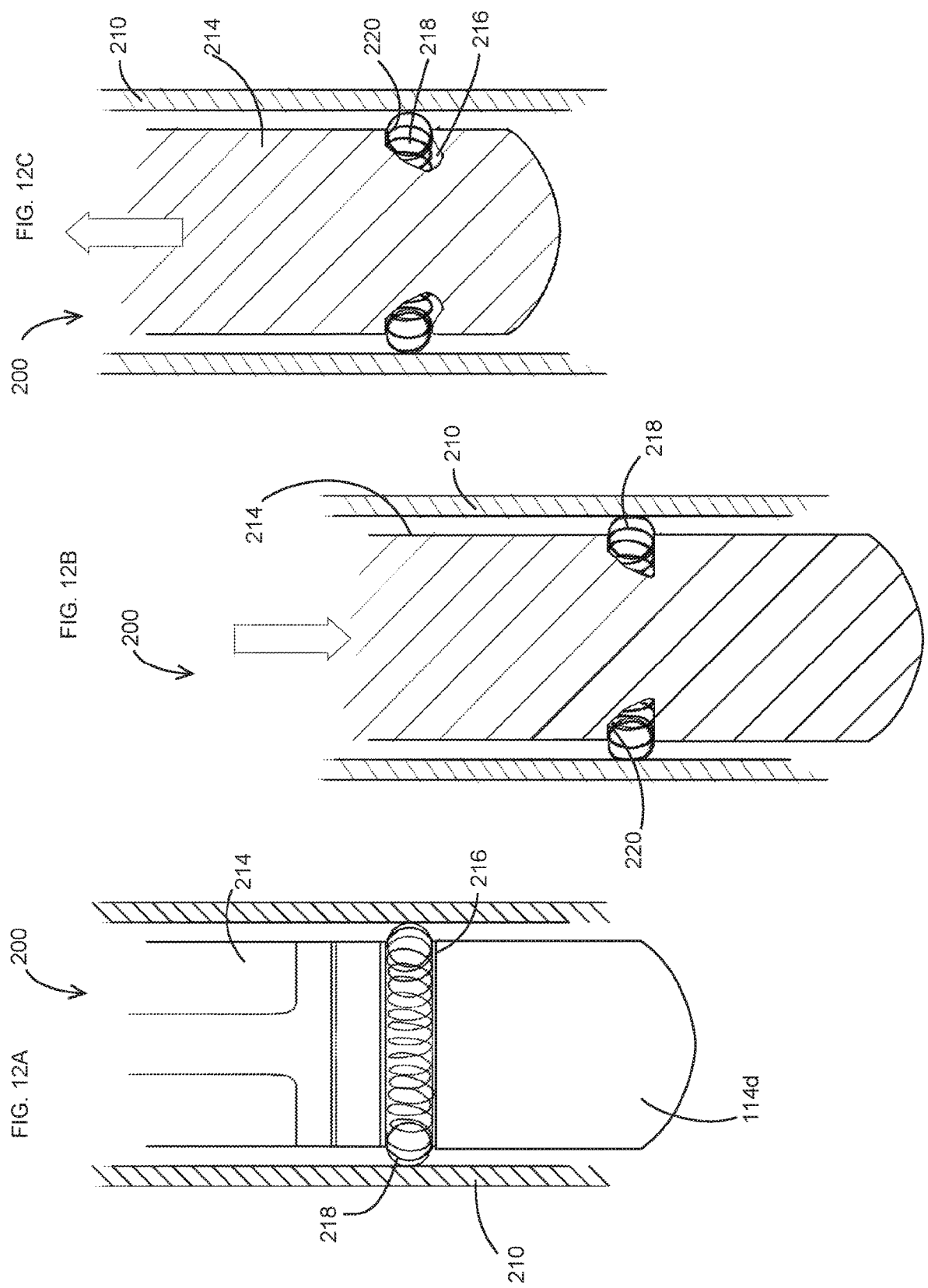
FIGS. 12A-C provide cross sectional views of a housing and a plunger embodiment as shown in FIGS. 8-9 during operation of the device.

The term "biasing member" as used herein includes springs of various types. In some embodiments herein, springs may include toroidal or annular springs which may include axial springs, radial springs, or cut length springs, in non-limiting examples. In one non-limiting embodiment, the spring may expand and contract to effect resistance on various portions of the device during movement thereof. In one non-limiting embodiment as shown in FIGS. 12A-C, the spring 218 may be housed within and/or movable relative to a groove 216. When the plunger 214 moves in a distal direction, the interface between the spring 218 and the outer housing 210 may increase, as the spring moves against the supra-groove surface 220, causing the spring 218 to expand or to deform, or both, in one example, such that additional resistance on the plunger 214 movement in the distal direction may be caused by an increased interface between the spring 218 and the housing 210 as seen in FIG. 12B. In many instances, the embodiments provided herein are applicable to autoinjector type training devices. However, in some instances, the embodiments described herein may be used in a manual injection device, or manual injection training device. Upon reset of the plunger, the spring 218 may move into the groove 216 as seen in FIG. 12C, relieving a portion of the resistance on the plunger 214 movement in the proximal direction, due in part, in some non-limiting embodiments, to the decrease in interface between the spring 218 and the device housing 210.

Figure 13:
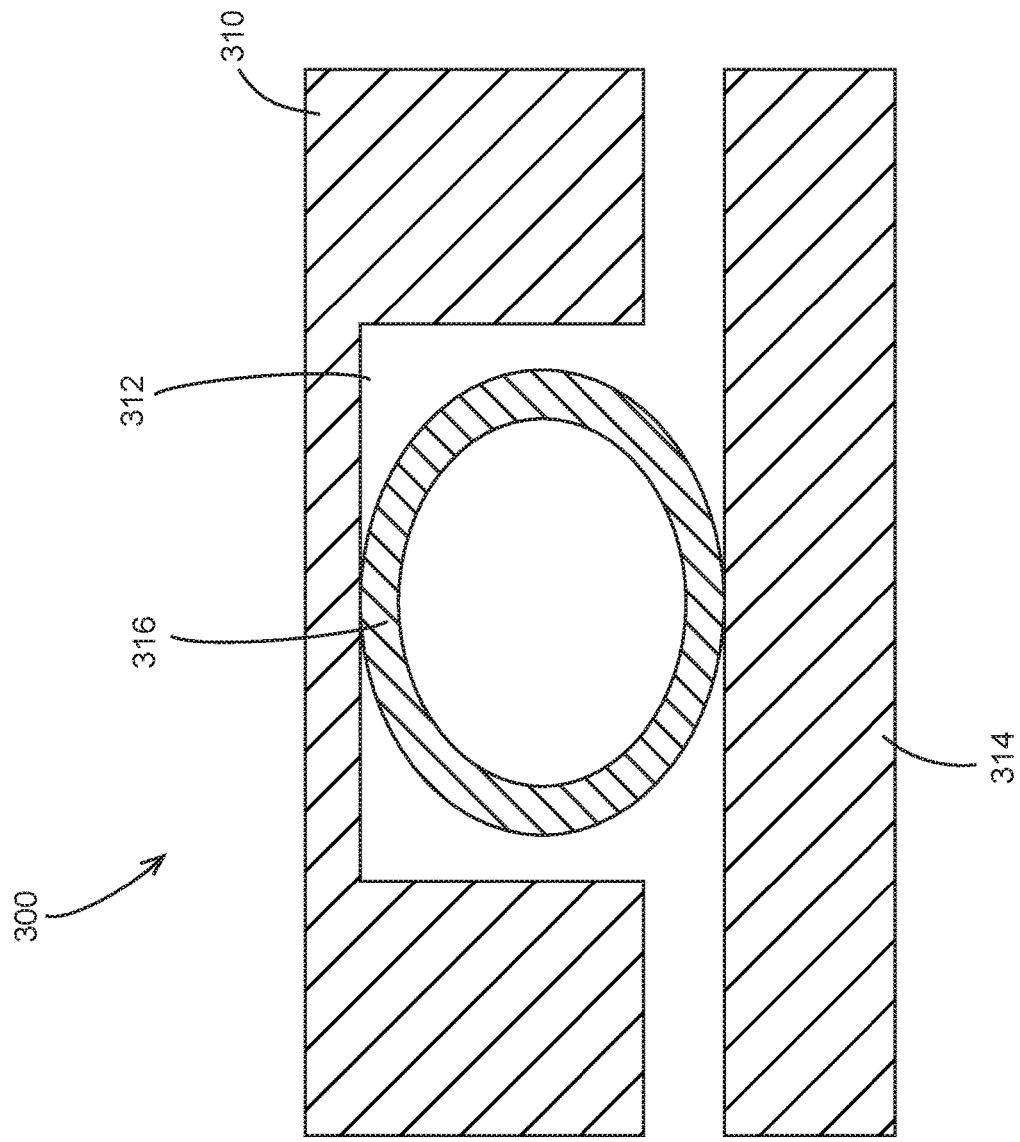
FIG. 13 provides a schematic view of an embodiment, wherein a portion of a housing includes a groove for housing a protrusion member therein.

In another embodiment 300 shown in FIG. 13, an injection simulation member embodiment 300 may include a housing 310, which may include a groove 312, and a protrusion member 316. The protrusion member 316 may include an annular member disposed within the groove 312 and moveable relative to the groove 312. In one non-limiting embodiment of the injection simulation device 300 as shown in FIG. 13, a friction between the annular member and a plunger 314 slidable relative to the housing 310 may increase upon movement of the plunger 314 in a distal direction as shown by the arrow in FIG. 13, increasing a resistance on the plunger 314 due to the interaction between the plunger 314, the annular member 316, and the groove 312. The groove 312 in FIG. 13 is shown with a relatively uniformly designed profile. In some non-limiting embodiments, the groove 312 profile may be provided such that resistance during movement of the plunger may be controlled as needed. For example, one portion of the groove 312 may be deeper than another portion, such that movement of the plunger in one direction may be easier than movement in the opposing direction. This may be due in part to the relative movement of the spring within the groove and/or in relationship to the plunger 314. In one non-limiting embodiment, the groove 312 may be constructed such that movement of the plunger 314 in one direction causes the annular member to fill the space of the groove 312 (in some embodiments, the annular member may deform to the shape of the groove 312), and in the opposing directional movement of the plunger 314, the spring may contract, or un-deform, to cause a differential resistance on the plunger 314 movement. AS shown in FIG. 13, the profile of the groove may be consistent. Different types of protrusion members, groove profiles, surface treatments of components within the device, and shape and profiles of the plunger and/or the housing can contribute to controlling the plunger movement, and in some instances, the plunger speed.

In an embodiment, a method of simulating a resistance of a autoinjector device may be provided, including, providing an injection simulation device having a housing and a plunger slidable or moveable relative to the housing, and a protrusion member at the interface between the plunger and the housing; and moving the plunger in a distal direction relative to the housing such that the protrusion member causes a resistance on the plunger movement to simulate resistance during an injection. In another embodiment, a method of controlling the resistance of a simulated injection with an injection simulation device may be provided. The method may include providing an injection simulation device 100, 190, 199, 200, 300, or 400, and increasing a viscosity of the fluid to increase the resistance on the distal movement of the plunger and decrease the resistance on the proximal movement of the plunger.

What is claimed is:

1. An injection simulation device for controlling the speed of a plunger movement, comprising:
    a housing defining an opening, and comprising a proximal end and a distal end;
    a plunger movable relative to the housing through the opening, the plunger comprising a first interfacing portion;
    a rotatable component positioned in the opening, said rotatable component defining a channel for receiving the plunger therewithin, the rotatable component axially rotatable around the longitudinal axis of the plunger, said rotatable component comprising a second interfacing portion configured to interface with the first interfacing portion during advancing or retracting of the plunger;
    a stationary component defining a cavity comprising a damping fluid, the cavity for receiving the rotatable component;
    wherein advancing the plunger in a distal direction through the opening causes rotational movement of the rotatable component around the circumference of the plunger, and within the opening of the housing, wherein that rotational movement is controlled by the damping fluid, increasing plunger resistance, and wherein retracting the plunger in a proximal direction decreases resistance on the plunger such that an increase in viscosity of the damping fluid decreases the speed of rotation of the rotatable component during distal movement of the plunger, and increases plunger resistance during distal movement.

2. The injection simulation device of claim 1, further comprising one or more sealing members disposed between the rotatable component and the stationary component to seal the fluid within the cavity.

3. The injection simulation device of claim 1, wherein one of the first interfacing portion or the second interfacing portion comprises a threaded portion and the other of the first interfacing portion or the second interfacing portion comprises a threaded receiving portion.

4. The injection simulation device of claim 1, wherein the damping fluid comprises a damping grease.

5. The injection simulation device of claim 1, wherein distal movement of the plunger increases an interface between the rotatable component and the stationary component.

6. The injection simulation device of claim 1, wherein proximal movement of the plunger decreases an interface between the rotatable component and the stationary component.

7. The injection simulation device of claim 1, further comprising a biasing member associated with the plunger.

8. The injection simulation device of claim 1, wherein an inner surface profile of the stationary component is complementary to an outer surface profile of the rotatable component.

9. A method of controlling the resistance of a simulated injection with an injection simulation device, comprising:
    providing the injection simulation device of claim 1; and
    increasing a viscosity of the fluid to increase the resistance on the distal movement of the plunger, wherein proximal movement of the plunger decreases the resistance on the plunger.

* * * * *